Feb. 8, 1966 H. M. TIRET Plant Pat. 2,599
FUCHSIA PLANT
Filed Nov. 18, 1964
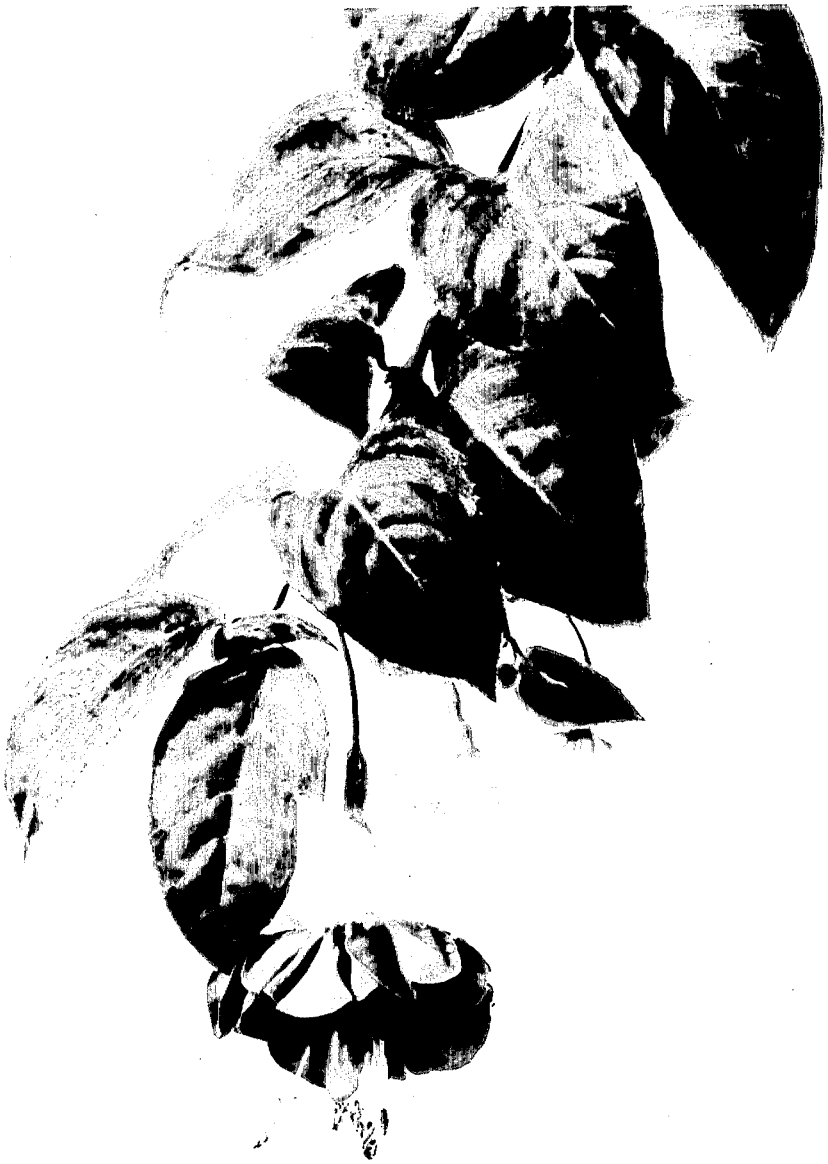

United States Patent Office

Plant Pat. 2,599
Patented Feb. 8, 1966

2,599
FUCHSIA PLANT

Horace M. Tiret, 2225 Taraval St.,
San Francisco, Calif.

Filed Nov. 18, 1964, Ser. No. 412,605
1 Claim. (Cl. Plt.—84)

This invention relates to a new and improved fuchsia plant, the principal new and different characteristic of which is the exceptional size of flower combined with contrasting new white sepals and deeply colored corolla, having an excellent trailing habit of growth, unlike any other fuchsia plant.

As a hybrid from a seedling (unpatented) not introduced to the trade, namely 14–42–1 and a seedling (unpatented) not introduced to the trade, namely 13–2–1, the figures representing applicant's own breeding symbols, the plant has been annually reproduced at Colma, California, by cuttings which retained the characteristics of the parent fuchsia.

The plant has a vigorous, trailing habit of growth. It is a heavy bloomer producing many large flowers. The petals are Bishop Violet (British Horticultural Color Chart #34). At the base of the petals they are marbled Camellia Rose (British Horticultural Color Chart #622).

In the accompanying drawing, the figure shows a typical branch tip, the drawing representing approximate actual size.

A detailed description of this new variety of fuchsia plant follows:

*Habit of growing.*—Trailing habit of growth, self-branching and an early bloomer.

*Foliage.*—The leaves are dark green, medium in size, with a slightly veined surface. The mature leaf is approximately 3½″ in length and 2″ in width at the widest point. The leaf is medium crinkly in texture. Branches are dark brownish-red.

*Buds.*—These are Veronese green when small (British Horticultural Color Chart #660–3) fading into white as bud matures. The length from ovary is approximately 1⅓″. Width at widest point is 1⅛″.

*Ovary.*—Solid green in color. Length, ½″, width at widest point 5/16″, at maturity.

*Sepals.*—Topside is white with green tips and shaded with Camellia Rose at the base and satiny texture. Underside is the same except for crepelike texture. Sepals are broad in form and are semi-curved. (Not fully recurved again tube.) They are four in number, 1¾″ in length and 1″ in width at widest point.

*Tube.*—Medium short. Length is approximately ¾″, width ⅜″ at widest point. The tube is white with shadings of Camellia Rose.

*Stamens.*—Eight in number, colored rose and maroon anthers. Medium slender, 1⅝″ in length.

*Pistils.*—The style is approximately 3″ in length from the ovary to its tip. In width it is 1/16″. The color is white with a creamy white stigma.

*Petals.*—The petals number 26 (approximately). They are exceptionally large, fully open corolla. The corolla is camellia-like in form when fully mature, giving a very symmetrical appearance. The diameter of the fully open mature flower is approximately 3″. The large mature petals are approximately 1¼″ in length and 1¾″ in width. They have a smooth appearance.

*Parentage.*—Applicant's own seedlings (unpatented) not introduced to the trade, applicant's breeding symbols 14–42–1 and 13–2–1.

Having thus disclosed my discovery, I claim:

A new and distinct variety of fuchsia plant herein described and illustrated, characterized by the exceptional size of the flower, attractive color contrast between corolla and broad semi-recurved sepals, and exceptional trailing habit, which constitute a fuchsia unlike any other of its type.

No references cited.

ABRAHAM G. STONE, *Primary Examiner.*